United States Patent [19]
Wilson et al.

[11] Patent Number: 6,165,741
[45] Date of Patent: Dec. 26, 2000

[54] METHOD FOR RAPID DETECTION OF BACTERIAL GROWTH IN CULTURES

[75] Inventors: David F. Wilson; Sergei A. Vinogradov, both of Philadelphia, Pa.

[73] Assignee: The Trustees of the University of Pennsylvania, Philadelphia, Pa.

[21] Appl. No.: 08/867,159

[22] Filed: May 30, 1997

[51] Int. Cl.$^7$ .......... C12Q 1/04; C07D 487/22; C09B 47/04; G01N 21/64

[52] U.S. Cl. .......... 435/34; 540/124; 540/140; 540/201; 436/172

[58] Field of Search .......... 435/34, 7.32, 64, 435/122, 252.1, 253.1; 540/124, 140, 201; 436/172

[56] References Cited

U.S. PATENT DOCUMENTS

| | | | |
|---|---|---|---|
| 4,062,727 | 12/1977 | Srinivasan et al. | 195/28 |
| 5,151,603 | 9/1992 | Nakamura | 250/458.1 |
| 5,164,301 | 11/1992 | Thompson et al. | 435/29 |
| 5,403,928 | 4/1995 | Arrhenuis | 540/128 |
| 5,418,301 | 5/1995 | Hult et al. | 525/437 |
| 5,523,214 | 6/1996 | Horn | 435/52 |
| 5,567,598 | 10/1996 | Stitt et al. | 435/29 |
| 5,652,106 | 7/1997 | Plikaytis et al. | 435/6 |
| 5,736,410 | 4/1998 | Zarling et al. | 436/172 |

FOREIGN PATENT DOCUMENTS

WO 95/10522   4/1995   WIPO .......... C07D 487/22

OTHER PUBLICATIONS

Leveidiotou, et al. Deltion Ellenikes Mikrobiologikes Etaireias, vol. 41 (6), pp. 603–607. (Nov.–Dec.1996).

Merriam–Webster's Collegiate Dictionary, 10th edition. Merriam–Webster, Inc., Sprinfield, MA. Pp. 449 and 874. (1996). No month given.

Jin et al. J. Chem. Soc. Chem. Commun. 16, pp. 1260–1262. (Aug.1993).

Vinogradov et al. J. Chem. Soc. Perkin Trans. 2. 1, pp. 103–111. (Jan.1995).

Griethuysen et al. J. Clin. Microbiol. 34 (10), pp. 2391–2394. (Oct.1996).

Leveidiotou, et al. STN, BIOSIS abstract, accession # 97:297146.

Boyle et al. Abstract U–141, in Abtracts of the 95th General Meeting of the American Society for Microbiology. American Society of Microbiology, Washington, D.C. p. 142. (1995).

*Primary Examiner*—Michael P. Woodward
*Assistant Examiner*—Marjorie A. Moran
*Attorney, Agent, or Firm*—Dilworth Paxson LLP; Evelyn H. McConathy

[57] ABSTRACT

This invention provides a method for growth detection and identification of microorganisms in a culture medium comprising providing a culture medium comprising a solubilized oxygen-quenchable phosphorescent compound, inoculating said culture medium with a substrate suspected of being associated with one or more microorganism, and detecting microorganism growth and identifying said microorganism by causing said phosphorescent compound to phosphoresce and observing quenching of oxygen in said culture of said compound.

18 Claims, 8 Drawing Sheets

METHOD FOR RAPID DETECTION OF BACTERIAL GROWTH IN CULTURES

FIELD OF THE INVENTION

The present invention refers to optical methods of monitoring and measuring the growth of microorganisms in cultural media, and more particularly, such methods which employ oxygen-quenchable phosphorescent compounds and dendritic polymeric derivatives of such oxygen-quenchable phosphorescent compounds.

BACKGROUND OF THE INVENTION

Methods for the detection and accurate measurement of the presence and growth progression of various microorganisms are useful for a variety of purposes, including monitoring yields in the production of microorganisms in industrial fermentation process and the early detection of pathogenic microorganisms.

Several methods are known, an example of which is U.S. Pat. No. 5,523,214. In this reference, there is described a method for visually demonstrating the growth of microorganisms in broths or gels such as fungi, yeasts and bacteria including mycobacteria, *M. tuberculosis, M. avium and M. bovis*, non-fermenters, cocci, bacilli, coccobacilli and enterobacteria obtained from urine specimens, matter from wounds and abscesses, blood and sputum and bacterial growth in broths or gels. In this reference, it has been estimated that relatively rapidly growing mycobacteria require approximately one week to demonstrate growth, and relatively more slowly growing tuberculosis agents such as *M. tuberculosis* and *M. bovis* and *M. avium*, which are known to appear in AIDS patients, require at least eight to ten weeks of incubation. To detect growth in this method, a mixture of indicators methylene blue and resazurin is added to the substrate or environment with care taken that not enough of the mixture be added to be toxic to the microorganisms. The substrate is iron (III) salts mixed with $K_3Fe(CN)_6$, iron (II) salts mixed with $K_4Fe(CN)_6$ or sodium tungstate ($Na_2WO_4$) As set forth in this reference, the mixture of indicators methylene blue and resazurin is said to demonstrate bacterial growth by changing color from blue to red more rapidly than resazurin alone. The method is also said to be improved by the addition of a redox stabilizer such as potassium hexacyanoferrate, $K_4Fe(CN)_6$.

As also related in this method, mixtures of inorganic salts of iron (III) such as $NH_4Fe(SO_4)_2$ and $K_3Fe(CN)_6$, or iron (II) such as $K_4Fe(CN)_6$, or $Na_2WO_4$ by itself are employed in culture media as redox indicators to demonstrate the growth of microorganisms.

Such a method is not commercially practical, however, as the amounts of redox indicators required to demonstrate microorganism growth are not consistently non-toxic, and/or require an inordinate amount of care to exclude toxic amounts to prevent false negative results. Such methods, as are all conventional methods, are not sufficiently sensitive to reduce the time required for demonstration of microbial growth from several weeks to a matter of days.

SUMMARY OF THE INVENTION

In the present invention, microorganism growth is rapidly and accurately demonstrated by inoculating, or otherwise contacting a culture medium comprising a solubilized oxygen-quenchable phosphorescent compound with a substrate suspected of carrying or associated with one or more microorganisms, and then detecting microorganism growth and identifying microorganisms by causing the phosphorescent compound to phorphoresce and measuring microorganism presence and growth by oxygen-dependent quenching of phosphorescence.

In accordance with this invention, a light source means, preferably a modulated light source, is employed for excitation of phosphorescence of the soluble phosphor in the microorganism-containing medium and determining both the phosphorescence intensity and delay time between the excitation light intensity and phosphorescence emission. Phosphorescence lifetime from the measured delay and/or intensity is calculated, followed by calculation of oxygen partial pressure (concentration) in the culture medium from oxygen dependence on the phosphorescence lifetime and appropriate calibration constants, i.e., quenching constant, and lifetime in the absence of oxygen.

The invention will be more fully understood from the following detailed description of preferred embodiments, drawings and examples, all of which are intended to be for illustrative purposes only, and not intended in any way to limit the scope or spirit of the claims of this invention.

DETAILED DESCRIPTION OF PREFERRED EMBODIMENTS

Figure 1:
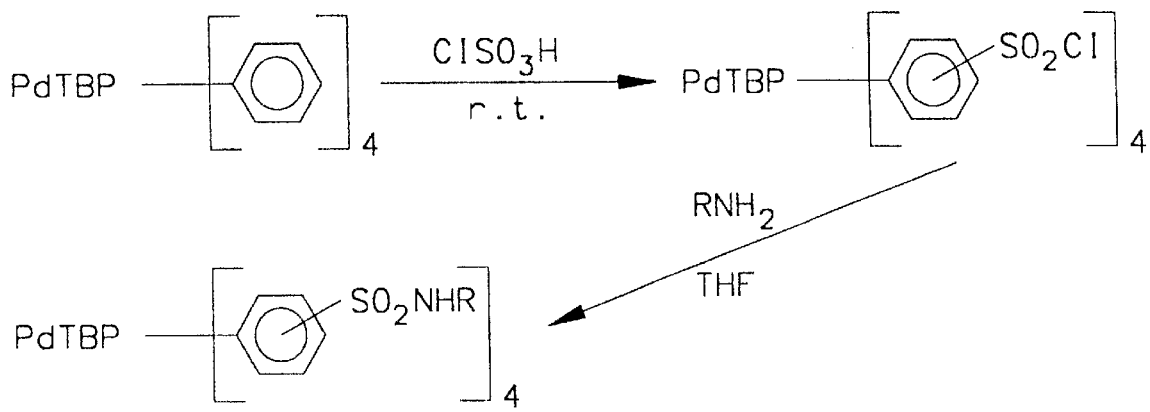
FIG. 1 illustrates an exemplary embodiment for the production of PdTBP and PdTPTPB functionalized derivatives, for initiating divergent dendrimer growth.

The present invention provides a process for the rapid and accurate demonstration of microorganism growth in a culture medium via inclusion in said culture medium of one or more non-toxic, water-soluble and/or otherwise physiological media-soluble phosphorescent compounds which measure oxygen content (partial pressure) by oxygen dependent quenching of phosphorescence in a culture medium.

One of the most effective methods of growing microorganisms is in a culture medium. An accurate measure of the rate of oxygen depletion in the culture medium can be used to determine not only whether growing organisms are present in the culture following inoculation, but also the rate of growth of that organism in the culture.

In the present inventive method, a very rapid determination of the presence of organisms such as mycobacteria is provided, as well as early indication of the type of organism present. For example, in the case of suspected tuberculosis patients, it is important to detect the growth of contagious organisms as early as possible to both treat the disease and to determine if isolation is required for the protection of other patients and health care staff.

The presence of growing organisms in a culture medium typically results in consumption of oxygen at rates above the rate of oxygen consumption in a sterile culture medium. Thus, the presence or growth of organisms in a culture medium can be determined from the relationship of the number of organisms present per unit volume of an incubation medium being proportional to the rate of depletion of oxygen from the medium.

Phosphorescence Measurement

In accordance with the present invention water-soluble, non-toxic phosphorescent compounds are admixed with or are otherwise solubilized within a culture medium. The culture medium can then be inoculated with microorganisms and thereafter exposed to a modulated light source for excitation of the phosphor to phosphorescence to allow determination of both the phosphorescence intensity and delay time between the excitation light intensity and phosphorescence emission. The phosphorescence lifetime from the measured delay and/or intensity is calculated as well as that of oxygen partial pressure (concentration) in the culture medium from the oxygen dependence on the phosphorescence lifetime with respect to a quenching constant and lifetime in the absence of oxygen.

Thus, the present inventive method provides an optical method of measuring oxygen concentration in culture media with high accuracy and precision.

Emitted light from an excited species which persists after excitation has ceased is referred to as phosphorescence, or afterglow. Phosphorescence of certain chemical compounds ("phosphors") is quenched by oxygen according to the Stern-Volmer relationship, which is stated as follows:

$$t_o/t = 1 + k_Q * t_o * PO_2 \quad (1)$$

where $t_o$ and t are the phosphorescence lifetimes in the absence of oxygen, $PO_2$ is the oxygen pressure for a lifetime of t, and $k_Q$ is the quenching constant. The constant $k_Q$ is related to the frequency of collisions between the excited triplet state molecules and molecular oxygen and the probability of energy transfer occurring when these molecules collide.

Phosphorescence may be measured by any available means in accordance with the present invention. In general, two conventional methods for measuring phosphorescence lifetime (or decay time) are the "pulse method" in the time domain, and the "phase method" in the frequency domain. In the pulse method, a sample is excited by a short pulse of light and the resulting phosphorescence emission in the longer wavelength is an exponentially decaying function with a measurable rate of decline. The pulse method is used in most of the existing instruments for oxygen measurement.

In the phase method, a sample is excited with modulated light, with absorbed light being re-emitted as phosphorescence after a certain delay period. As a result phosphorescent emission is also modulated with the same frequency but delayed in time (phase shifted) with respect to the excitation sinusoid. This phase shift, found experimentally, is used to calculate the phosphorescent lifetime.

The phase method is preferably used in the present invention due to the advantages that (i) frequency lock amplification can be used to greatly increase sensitivity and (ii) interference from ambient light is greatly decreased since only singles with the same modulation frequency as the excitation light is amplified, which largely eliminates interference by other ambient light sources.

In the phase approach, the mathematical relationship between phase shift and phosphorescence lifetime can be described as follows:

$$\tan \phi = 2\pi f t \quad (1)$$

where
$\phi$=phase difference (phase shift) between excitation and emission sine waves at the modulation frequency f
t=lifetime of phosphorescent decay It can be shown that for a given signal-to-noise ratio, the lowest error in the estimation of the phosphorescence lifetime can be obtained when phase shift is about 35.3°.

For example, with the phosphor Pd-meso-tetra(4-carboxyphenyl)porphyrin bound to bovine serum albumin (phosphors are discussed in detail infra), $t_o$ at 38° C. equals 646 µsec and the lifetime at air saturation is 16 µsec. The physiologically important range of oxygen concentrations extends from zero to approximately 150 Torr (air saturation). If follows from the Stern-Volmer relationship (1) and equation (2) that to maintain the phase shift of about 35.5° for all oxygen concentrations in the range, it is necessary to be able to vary the modulation frequencies from 100 Hz to 2000 Hz. It is preferably to control modulation frequencies from 20 Hz to 20,000 Hz, and to employ instrumentation which can measure phosphorescence lifetime of a given fixed frequency and/or at a first estimate optimal frequency for a given value of the phase shift (35.5°), and to then proceed with actual lifetime measurement. To ensure oxygen measurements are accurate to air saturation and above (lifetimes <30 msec), the phosphorescence signal is preferably sampled (digitized) at 37.5 kH$_2$ or greater.

A preferred instrument for practice of the present invention can be constructed from Analog Devices ADSP-2181 and AD 1847 Stereo Codec with stereo high precision 48 kHz, 16 bit, Delta-Sigma ADCs with 64×oversampling.

Generation of the Variable Frequency (20 Hz to 20 kHz) Sinusoidal Modulation of Light Output from Light-Emitting Diodes A sine wave signal of the desired frequency can be generated by the DSP using a 16 bit DAC and smoothing circuits of the Stereo Codec, and this signal will control the current in the LED or laser diode driving circuit. The LED driver circuit is designed to provide a greater than 90% modulation of light output. This is accomplished by adding a DC signal to the sinusoidal signal such that the minimum current is just above the threshold for light emission. Above this threshold, the light output is a nearly linear function of the current through the LED.

Light-emitting diodes (LEDs) can be used as excitation sources. LEDs provide monochromatic light with a relatively broad bandwidth. This light is preferably passed through an interference filter to block the long wavelength "tail" in the emission of the LED, which otherwise might interfere with the measurements.

Measuring Phosphorescence Emission

The phosphorescence is collected, passed through appropriate filters and carried to the detector. The photodetector (PD) can be either a silicon photodiode with a built-in preamp or a photomultiplier. The photodetector output is amplified to provide a signal of optimal voltage for digitizing by the ADC. The photodiodes with an internal amplifiers are selected for the optimal light sensitive surface area and lowest noise level. The OPT202 unit (Burr-Brown) has an appropriate surface area (more than 5 mm2) and excellent photosensitivity, about 500 mV/mW for the 600 to 850 nm wavelength range and is preferred for use in the present invention. The signal from the photodiode can be further amplified with an AC-coupled operational amplifier. The quality of the phase detection depends on the reduction of noise level in the photodiode output signal. After amplification, the photodiode output signal is delivered to the analog multiplexer and then to the input of the 16 bit, 48 kHz Delta-Sigma digitizer, such as a 16 bit analog-to-digital converter (ADC) and digitized. The digital signals will be processed to extract the signal strength (magnitude) and phase relative to the excitation light. Calculations of the phosphorescent lifetime and oxygen pressure will follow above-described procedures.

MICROORGANISMS

As set out above, this invention is based on the measurement of the quenching effect of the partial pressure of oxygen (oxygen concentration) available in a culture medium to determine the presence and amount of microorganism present in the medium. The method of this invention is useful in demonstrating the presence and growth of any oxygen depleting microorganism, identifying the microorganisms and testing them for sensitivity to antibiotics by measurement of oxygen partial pressure via phosphorescence emitted by soluble, oxygen-quenchable phosphorescent compounds (phosphors). The microorganisms may be from such sources as urine specimens, matter from wounds and abscesses and blood, tissue and sputum samples, and be present in gels or broths with various substrates along with one or more phosphors. Exemplary bacteria include species from the genera Bacillus, Mycobacterium, Actinomyces, Nocardia, Pseudomonas, Methanomonas, Protaminobacter, Methylococcus, Arthrobacter, Methylomonas, Brevibacterium, Acetobacter, Micrococcus, Rhodopseudomonas, Corynebacterium, Microbacterium, Achromobacter, Methylobacterium, Methylosinum, Methylocytis, Acinetobacter, and mixtures thereof. The rapid detection attributes of the present invention reduce the time typically required for growth demonstration/identification of, for example, mycobacteria from approximately several weeks to less than a week or a matter of days. The inventive method is particularly suited for the rapid growth demonstration of about several days of such slow growing tuberculosis agents as *M. tuberculosis* and *M. bovis* and the *M. avium* which appears in AIDS patients, all of which require at least eight to ten weeks of incubation for growth demonstration by conventional methods.

The inventive method is also useful in monitoring the production of microorganisms in fermentation processes which are widely use for a variety of purposes including chemical conversions, protein preparation, chemical reactions/chemical compound production, examples of which are discussed in U.S. Pat. No. 4,226,989.

Water-Soluble Oxygen Quenchable Phosphorescent Compounds

Water soluble oxygen-quenchable phosphorescent compounds (phosphors) useful in the present invention, and which are currently employed in methods for determining tissue oxygen concentration/oxygen partial pressure by measuring the quenching effect of oxygen on molecular phosphorescence of organic compounds are described, for example, in U.S. Pat. No. 4,947,850, which is incorporated herein by reference. In such phosphors, the phosphorescent chromophor, e.g., PdPorph and PtPorph is the phosphorescent portion of the phosphor that can be converted to the triplet state (T.) by light absorption, followed by a return to the ground state by light emission, or phosphorescence.

For phosphors to be suitable for use, inter alia, in determination of microorganism growth and identification in the present invention, the phosphors should be non-toxic to microorganisms or of negligible toxicity, and should also be of sufficient solubility in culture media such that oxygen molecules can approach close enough for efficient quenching to provide for reliable and accurate oxygen measurements, and the measurement of microorganism growth.

A new class of phosphors particularly suitable for oxygen measurement and concomitant microorganism growth identification in accordance with this invention has recently been reported in Vinogradov and Wilson, *J. Chem. Soc., Perkin Trans.* 2: 103–111 (1995), and in U.S. application Ser. No. 08/767,158, now U.S. Pat. No. 5,837,856, which is a continuation in part of U.S. application Ser. No. 08/137,624, filed Oct. 15, 1993 which are incorporated by reference herein, both of which are complexes of Group VIII metals, such as Pd and Pt, with extended porphyrins, such as, for example, tetrabenzoporphyrin, tetranaphthaloporphyrin, tetraanthraporphyrin and various derivatives thereof. Pd complexes of tetrabenzoporphyrins and tetranaphthaloporphyrins are especially desirable. Further, Pd tetrabenzoporphyrins (PdTBP) and their derivatives have been shown to have long-lived phosphorescence (~250 msec) with quantum yields of 8–10%.

More preferred for use in the present invention are dendritic derivatives of the aforementioned phosphors which are highly efficient and highly soluble phosphorescent compounds which are surrounded by an inert globular structure, an example of which is derivatized PdTBD surrounded by three-dimensional supramolecular structure known as a dendrimer. Such compounds are described in U.S. application Ser. No. 08/767,158, filed Dec. 16, 1996, now U.S. Pat. No. 5,837,865, the entirety of which is incorporated herein by reference.

Dendrimer phosphors useful in this invention are three-dimensional supramolecular radial symmetrical molecules comprised as an initiator functionalized core, which in the present invention are oxygen-measuring phosphors, with interior layers attached to the core which are comprised of, for example, three or four arms with each arm being composed of repeating units, and with the layer of repeating units in each arm considered to be a generation of the dendrimer. The outermost generation typically contains terminal functional groups, such as a primary amine attached to the outermost generation. The size and shape of the dendrimer molecule, and the functional groups present therein can be controlled by the choice of the initiator core, the number of generations, and the nature of the repeating units employed at each generation. For example, the chemical functionality of the repeating units in the interior layers can be amidoamines, such as diethylene diimine, and with terminal functionalities, such as, for example, amino groups, hydroxyl groups, carboxylic acid groups, carboxylates and the like. See Urdea et al., *Science* 261: 534 (1993) and Frechet, 263: 1710–1715 (1994). Thus, dendrimers are combinations of monomeric units which allow branching at each step of polymerization. As shown, for example, by Blumen et al., *Angewandte Chemie, Int.,* Ed. Eng. 29: 113–125 (1990), dendrimers tend to form globular structures with increasing numbers of monomeric units, which eventually will cover the centralized functional entity or compound. See also, for example, Winnik et al., U.S. Pat. No. 5,256,193.

At least two methods are known for the synthesis of dendrimer polymeric structures: the convergent and divergent growth approaches, respectively. Both are contemplated for use for the production of phosphors for use in the present invention.

In the convergent dendrimer synthetic route, polymer synthesis is initiated from the periphery and ends by linking branched fragments to a central core. For a detailed description of the convergent synthetic method, see Hawker et al., *J. Am. Chem. Soc.* 114: 8405–8413 (1992), Wooley et al., *J. Chem. Soc. Perkin Trans.* 1: 1059–1076 (1991), and Frechet et al., U.S. Pat. No. 5,041,516, all of which are incorporated herein by reference.

It has recently been reported that the convergent synthetic route is useful in the modification of porphyrins, i.e., producing a dendritic molecule with a core having photochemical functionality. See, Jin et al., *J. Chem. Soc. Chem. Commun.* 1260–1262 (1993). This reference describes measuring quenching of fluorescence of a Zn porphyrin encapsulated in a dendritic cage, and that the dendrimer polymeric structure provides good protection for the porphyrin core, serving as a barrier for large molecules while allowing access to smaller species.

The more typically used divergent synthetic method employs a reverse order of synthesis which involves an initial reaction of a monomer with an initiator core, followed by successive reaction of the resulting functional groups with a difunctional compound, such as a diamine, to provide the next generation of reactive amino groups such that layers of monomeric units are added to a central core sequentially until the desired degree of branching is achieved. A detailed explanation of this method can be found, for example, in Tomalia et al., *Angewandte Chemie, Int.,* Ed. Eng. 29: 138–175 (1990) and Tomalia et al., *Macromolecules* 19: 2466–2468 (1986), which are also incorporated by reference herein.

Other references relating to dendritic macromolecules and their methods of production can be found in U.S. Pat. Nos. 5,418,301; 4,568,737; 5,393,795; 5,256,193; 5,393,797; 5,393,795; 5,393,797; 5,098,475; 5,041,516 and 4,568,737, the entire disclosures of which are incorporated herein by reference.

As described below, in one aspect of this invention, one-, two-, and three-layer polyglutamate dendritic cages synthesized divergently around novel derivatized metallo extended porphyrin oxygen-measuring phosphor compounds results in phosphors which are highly water-soluble in a wide pH range and display narrow distribution of phosphorescence lifetimes in deoxygenated water solutions.

As further shown below, the combination of the novel phosphor derivatives with dendrimers which are used as the phosphor's surrounding environment, provides a novel class of phosphorescent probes for accurate and reliable oxygen measurements in culture mediums for reliable and fast culture growth demonstration and identification.

The dendritic phosphors are prepared from phosphors described in copending U.S. application Ser. No. 08/137,624 and Vinogradov and Wilson, *J. Chem. Soc., Perkin Trans.* 2: 103–111 (1995), and preferably are of the following formula:

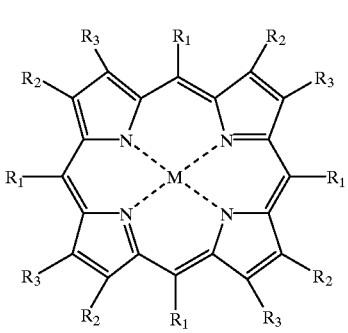

I where $R_1$ is hydrogen or substituted or unsubstituted aryl; $R_2$ and $R_3$ are independently hydrogen or are linked together to form substituted or unsubstituted aryl; and M is $H_2$ or a metal. When $R_2$ and $R_3$ are linked together to form an aryl system, the aryl system is necessarily in a fused relationship to the respective pyrrole substrate.

M is preferably a metal selected from the group consisting of Lu, Pd, Pt, Zn, Al, Sn, Y and La, and derivatives thereof, with Pd, Pt and Lu being most preferred. Non-limiting examples of suitable metal derivatives include, Pd tetrabenzoporphyrin (PdTBP), Pd tetraphenyltetrabenzoporphyrin (PdTPTBP), and PtTBP, PtTPTBP, LuTBP and LuTPTBP and naphthaloporphyrins, such as, for example, LuTNP and PdTPTNP, all of which are described in U.S. Ser. No. 08/137,624.

In certain preferred embodiments, the phosphors are tetrabenzoporphyrin (hereinafter "TBP") compounds, which correspond to the compound of formula I above wherein vicinal $R_2$ and $R_3$ groups are linked together to form benzene rings which are fused to the respective pyrrole rings. Also preferred are tetranaphthoporphyrin (hereinafter "TNP") and tetraanthraporphyrin (hereinafter "TAP") compounds wherein vicinal $R_2$ and $R_3$ groups are linked together to form naphthalene and anthracene ring systems, respectively. As with the fused benzene rings, the naphthalene and anthracene ring systems are fused to the respective pyrrole rings.

Unless indicated otherwise, or unless apparent from the disclosure, further reference herein to "TBP" compounds is understood to refer also to TNP and TAP compounds.

Preferred TBP compounds have the following formula

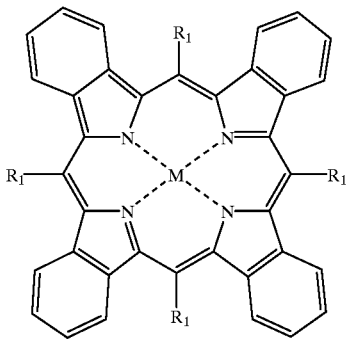

II wherein $R_1$ and M are as defined above. Particularly preferred TBP compounds are metallotetrabenzoporphyrin (hereinafter "MTBP") compounds where M is a metal or metal derivative as described hereinbefore.

Particularly preferred among the TBP compounds are the compounds of formula IV above where at least one of $R_1$ is substituted or unsubstituted phenyl. These compounds are referred to hereinafter as phenyltetrabenzoporphyrin (hereinafter "PhTBP") compounds. Preferred PhTBP compounds include substituted or unsubstituted tetraphenyltetrabenzoporphyrin (hereinafter "TPTBP") compounds, including meso-tetraphenyltetrabenzoporphyrin (hereinafter "m-TPhTBP") compounds, which have the following formula:

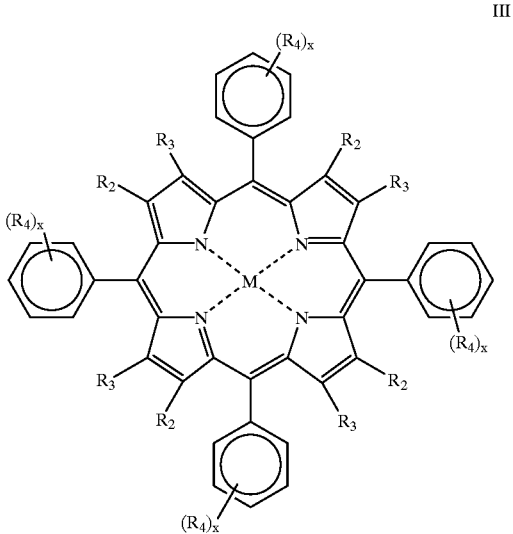

III where $R_2$, $R_3$ and M are as defined above, $R_4$ is a substituent group, and x is an integer from 0 to 3. Particularly preferred TPTBP compounds are substituted compounds of formula V where x is an integer from 1 to 3.

With respect to preferred substituted compounds of the invention, substituent groups are desired which impart such desirable properties to the compounds as solubility in polar solvents, including aprotic solvents, such as dimethylformamide (DMF), acetone and chloroform ($CHCl_3$), and protic solvents, such as water. The degree of substitution and the nature of the substituent groups may be tailored to obtain the desired degree of solubility and in the desired solvent or solvent mixture.

Example Preparation of Dendrimer Phosphors

A preferred synthetic preparation of the phosphors for use in the present invention is now illustrated. First, synthesis of PdTBP derivatives with chemically active functional groups is carried out to allow for further addition of dendritic fragments. Next, the actual layer-by-layer divergent growth of the dendrimer polymeric structure around the porphyrin core is accomplished to form the completed probe.

An alternate embodiment of convergent synthesis of the branched dendritic fragments, followed by attachment to a control porphyrin moiety is also contemplated.

Functionalizing a (Pd)TBP into (Pd)MCTBP

TBP and tetraphenyltetrabenzoporphyrins (TPTBP) for use in this invention can be synthesized by the template condensation of potassium phthalimide with phenylacetate in the presence of Zn salts, according to the method reported by Kopranenkov et al., *J. Gen. Chem.* (Russ.) 51: 2165–2168 (1981) and Ichimura et al., *Inorg. Chim. Acta.* 182: 83–86 (1991). Tetratoluyltetrabenzoporphyrin can also be synthesized in approximately 10% yield by using 4-methylphenylacetate as a condensing agent. See, for example, Kopranenkov et al. (1981). However, as both TBP and TPTBP compounds do not contain functional groups suitable for further modification, functional groups must be added to the formed TBP and TPTBP structures.

General approaches for modification of TBP and TPTBP in accordance with this invention include a) electrophilic substitution (chlorosulfation, nitration, etc.) of phenyl rings in TPTBP's, and b) electrophilic substitution, such as nitration, of meso-positions of non-substituted TBP followed by reduction and attachment of 1,3,5,-tricarboxylic acid fragments.

It is known that phenyl rings of TPTBP and PdTPTBP are most active in electrophilic substitution reaction. See, for example, Vinogradov and Wilson, *J. Chem. Soc., Perkin Trans.* 2: 103–111 (1995). Such reactions, however, are not always very selective and can lead to non-selectively modified probes, with substitution occurring in either the ortho- or para-positions of phenyl substituents, with the resulting production of a variety of regio- and stereo-isomers which are present in the reaction products. As exemplified below in FIG. 1, chlorosulfation of PdTPTBP leads to a mixture of tetra substituted chlorosulfonate-PdTPBP, each of which can then react with different amines to initiate divergent dendrimer growth.

It has also been shown that PdTPTBP can be readily chlorosulfated and converted into the corresponding sulfonamide with aminopolyethyleneglycols. See Vinogradov and Wilson (1995).

Figure 2:
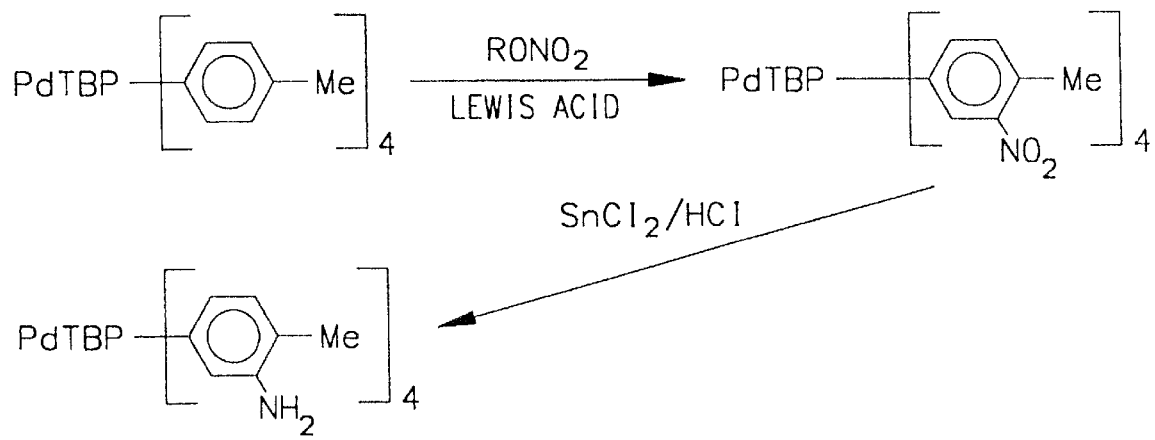
FIG. 2 illustrates another exemplary embodiment for the production of PdTBP and PdTPTBP functionalized derivatives for initiating divergent dendrimer growth.

In accordance with this invention, it is also contemplated that the employ of phenyl rings substituted with methyl groups will significantly decrease the number of isomers formed in electrophilic substitution due to stearic restrictions, especially when soft electrophiles are used for modification, thereby increasing selectivity. Therefore, in accordance with this invention it is contemplated that nitration of Pd tetratoluyltetrabenzoporphyrin with agents such as esters of nitric acid in presence of weak Lewis acids such as $LnCl_3$, $ZnCl_2$ or zeolites will lead to only one regioisomer, Pd tetra(4-methyl-3-nitrophenyl) tetrabenzoporphyrin. This can then be reduced to the corresponding amino derivative (FIG. 2). Separation of the stereoisomers can be performed chromatographically and methods have been described previously for meta- and orth-tetra-amino-phenylporphyrins. See Rose et al. "Large-scale preparation of α, β,α',β'-atropoisomer of meso-tetrakis (0-aminophenyl) porphyrin, *J. Org. Chem.*, 58: 5030–5031 (1993).

Figure 3A:
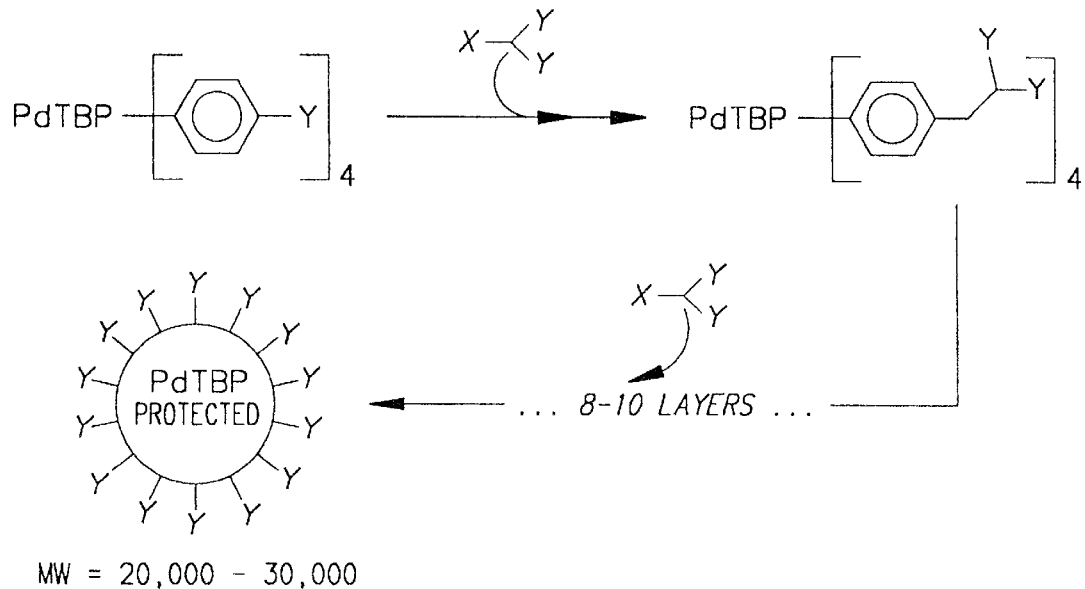
FIG. 3a illustrates the production of dendrimer growth on a core functionalized porphyrin with functional groups located at the para-positions of meso-phenyl rings.

Molecular-mechanics simulations carried out with MacroModel (Unix Version 3.5, MM2 force field) in accordance with that reported in Mohamadi et al., *J. Comput. Chem.* 11: 440 (1990) show that 6–10 layers of monomeric units, such as glutamates, are preferably added to a porphyrin if the initial functional groups are located at the para-positions of meso-phenyl rings to desirably achieve good protection of the central porphyrin fragment using the divergent synthetic approach (see FIG. 3A). This leads to molecules with molecular weights of about 14,000–30,000 Daltons. However, such large species might not be very useful in practice because of difficulties in excretion from the blood stream.

Figure 3B:
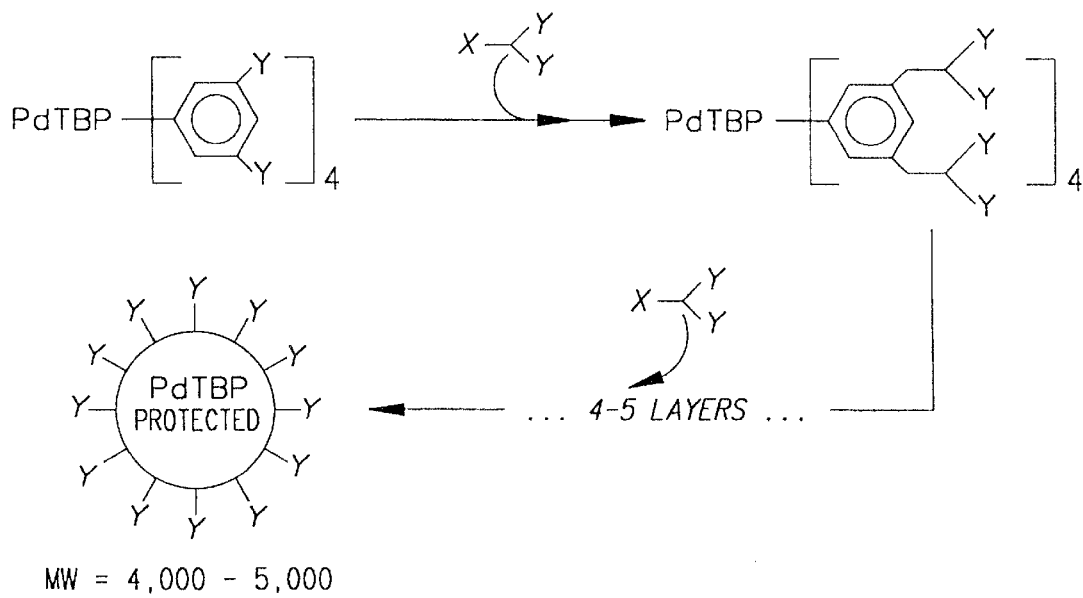
FIG. 3b illustrates the production of dendrimer growth on a core functionalized porphyrin with functional groups located at the meta-positions of meso-phenyl rings.

Further experimental data has shown that three layers decreases the oxygen quenching constant from near $2 \times 10^3$ Torr$^{-1}$ sec$^{-1}$ to about 750 Torr$^{-1}$ sec$^{-1}$. The latter is similar to that observed for the porphyrin bound to albumin and is suitable for measurements in vivo. Thus, it is preferable that up to four layers of glutamate will be sufficient for achieving an optimized oxygen probe. In any case, molecular modeling shows that if dendrimer growth starts from the meta-positions, globular structures form much faster and only three to five layers of monomers are needed for generation of a fully globular structure (see FIG. 3b). In this case, the molecular weight of the probe molecules will be between about 4,000 and 5,000 Daltons, which is a desirable size for good penetration through the kidney filters. Thus, it is preferred that functional groups be introduced selectively into the meta-positions of the meso-phenyl substituents. However, it is contemplated that the porphyrin moiety will direct electrophilic substitution to the para- and orth-positions of the phenyl rings.

Figure 4A:
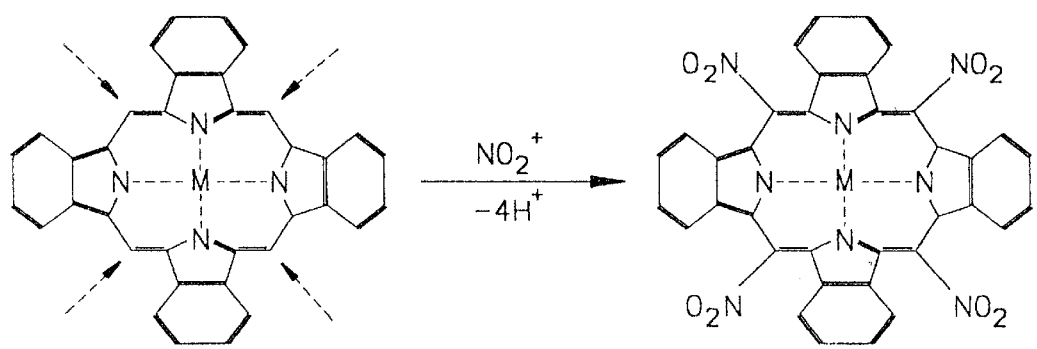
FIG. 4a illustrates a preferred embodiment of the invention of the production of a functionalized PdTBP with meta- (or psuedo meta-) functional groups by direct nitration of non-substituted TBP into meso-positions to produce (Pd) teranitrotetrabenzoporphyrin (PdTNTBP).

In a further embodiment of this invention, another reaction pathway to achieve formation of PdTBP with meta- (or pseudo meta-) functional groups is provided. This reaction is based on the direct nitration of non-substituted TBP into meso-positions, (see FIG. 4a). As shown in FIG. 4a, the arrows indicate the most probable direction for electrophilic attack. Direct nitration of porphyrins is known. See Drach et al., *J. Org. Chem.* 39: 3282–3284 (1974) and Bonnet et al., *J. Org. Chem.* 30: 2791–2798 (1965). The direct nitration of ZnTBP is also known. See Kopranenkov et al., *Chem. Heter. Comp.* (*Russ.*), 960–964 (1986). As shown in this reference, by using HNO$_3$/acetic acid and HNO$_2$/trifluoroacetic acid, up to four nitro groups can be introduced into the meso-positions of TBP cycle with yields of up to 11%.

It is also contemplated in this invention that strong ionic nitrating agents, such as, for example, BF$_4$NO$_2$ or highly activated covalent nitrating systems, such as, for example, AcONO$_2$/BF$_3$.ET$_2$O and RONO$_2$/TiCl$_4$ be employed to increase both overall yield of nitration and the relative yield of tetranitrotetrabenzoporphyrin (TNTBP). Nitration can be carried out at the earliest state of transformation when TBP is present as its Zn complex.

Figure 4B:
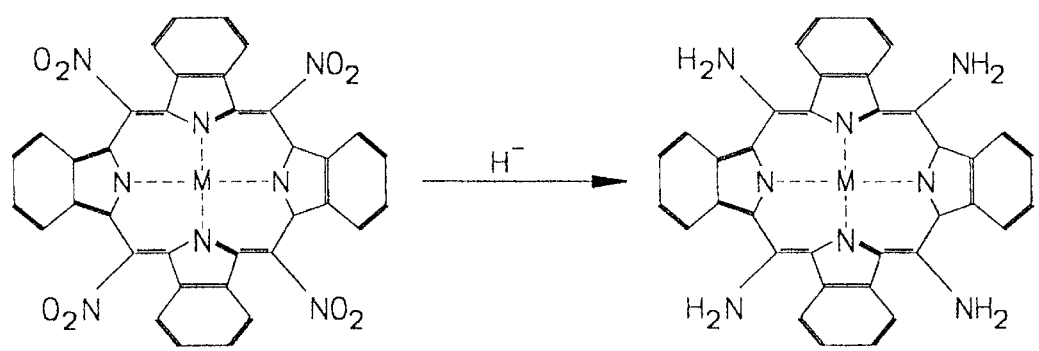
FIG. 4b further illustrates the preferred embodiment of the functionalized core porphyrin of FIG. 4a by the transformation of (Pd)TNTBP into the corresponding tetraminotetrabenzoporphyrin (TATBP or PdTATBP).

It has also been found that Zn tetranitrotetrabenzopophyrins (meso-TNTBP) can be easily demetallated by using AcOH/H$_3$PO$_4$ and that the insertion of Pd into TNTBP proceeds faster than into non-substituted TBP, which is due to increased non-planarity of the tetranitrated macrocycle, as confirmed using molecular-mechanics calculations (MacroModel V.3.5, MM2 force field). The reduction of TNTBP (or PdTNTBP) into corresponding tetraaminotetrabenzoporphyrin (TATBP or PdTATBP) is shown in FIG. 4b. In accordance with this invention, the resulting TATBP can be produced in good yield by preferably employing systems with increasing reducing activity, such as Zn/HCl, SnCl$_2$/AcOH, Na/MeOH, NaBH$_4$/MeOH, LiAlH$_4$/THF.

Figure 4C:
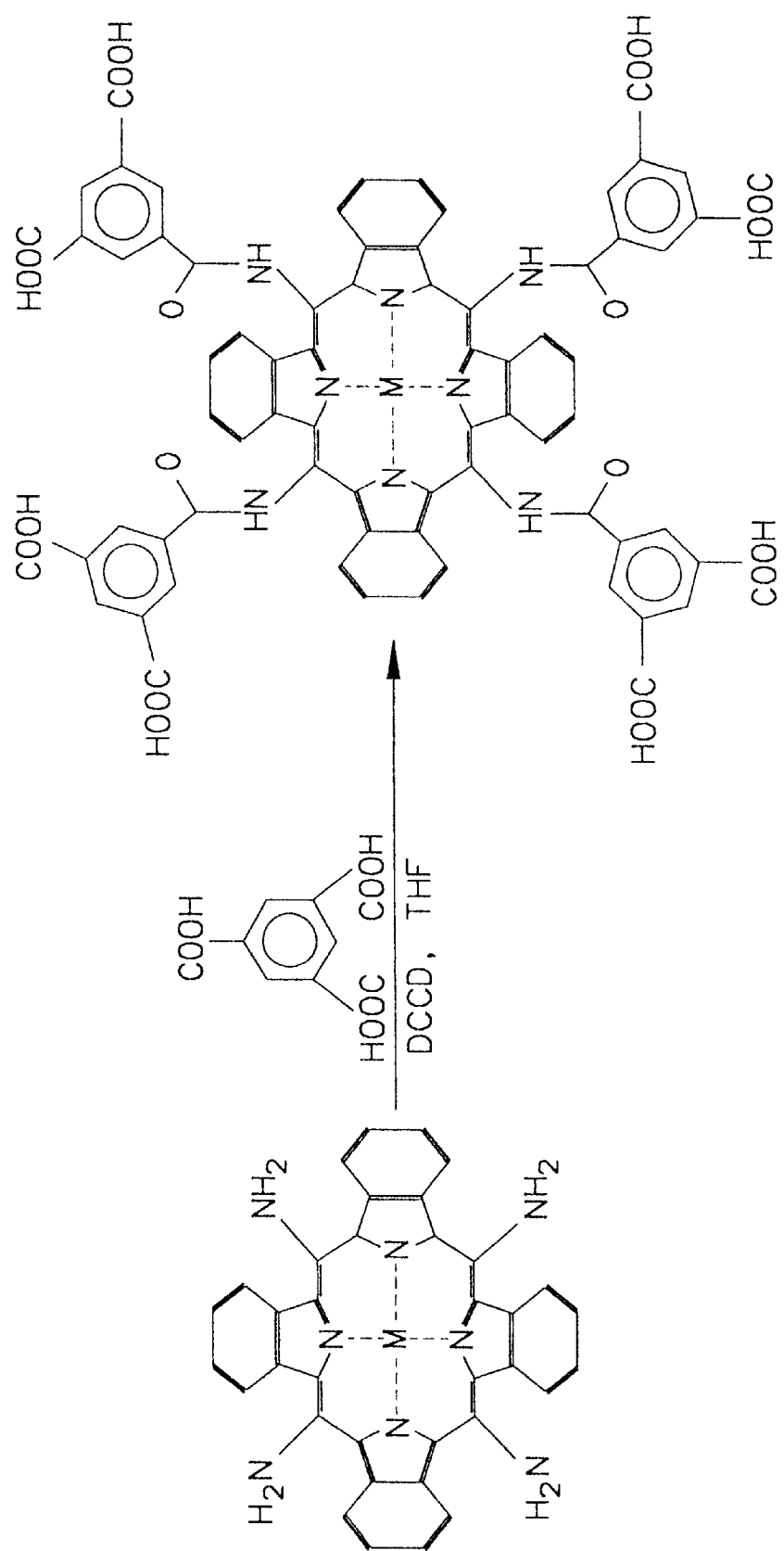
FIG. 4c further illustrates a preferred embodiment of the invention by additional functionalization of TATBP or PdTATBP in FIG. 4b with 1, 3, 5-benzenetricarboxylic acid to produce (Pd) metacarboxytetra-benzoporphyrin (MCTBP or PdMCTBP)

After formation of TATBP, further derivatization can be achieved by any of several methods employing high reactivity of the amino groups. A preferred method is amide formation between 1,3,5-benzene-tricarboxylic acid and TATBP (or PdTATBP) carried out in the presence of dicyclohexylcarbodiimide (DCCD) to produce a TBP containing pseudo meso-phenyl substituents with metacarboxyl groups, or as termed herein, metacarboxytetrabenzoporphyrin (MCTBP). In accordance with this preferred illustrative embodiment, MCTBP, or its Pd derivative, as shown below can be used as a core for dendritic polymer growth. See FIG. 4c.

In yet another aspect of this invention, a preferred direct synthesis of functionalized porphyrins is provided which leads directly to substituted TPTBP with chemically active functionalities and suitable as a core for dendritic polymer growth. As discussed hereinabove, tetrabenzoporphyrins, TBP, and tetraphenyltetrabenzoporphyrins, TPTBP, are generally synthesized by template condensation of potassium phthalimide with sodium acetate or sodium phenylacetate in the presence of Zn salts. However, due to the harsh conditions required for the template condensation, functional groups in either phthalimide or phenylacetic acid fragments usually do not survive. In accordance with the present invention, it has now been found that under modified conditions, meso-p-Br-phenyltetrabenzoporphyrins (PdTBrPTBP) and meso-p-Cl-phenyltetrabenzoporphyrins (PdTClPTBP) can be synthesized directly from bromo-and chloro-phenylacetic acids. These compounds can then be converted to reactive functionalized TPTBP's by means of Pd-catalyzed cross-coupling and catalytic carbonylation. For example, with Pd catalysis, PdTPhTBP's containing Br-substituents can be converted into corresponding carboxyl compounds as follows:

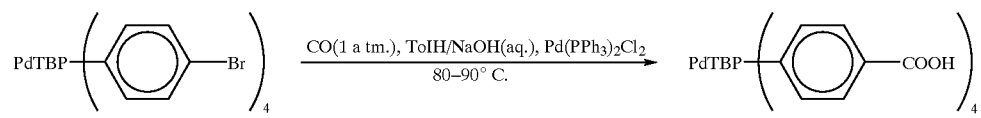

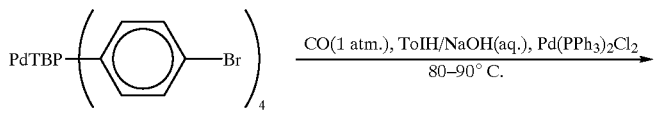

-continued

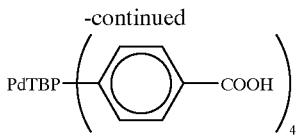

Catalytic reactions, including carbonylation and cross-coupling, for transformation of aryl halides into more reactive aryl derivitives are discussed in Colquhoun et al., "Carbonylation: direct synthesis of carbonyl compounds", Plenum Press, New York, (1991) and Heck, "Palladium reagents in organic synthesis", Academic Press, New York, (1985).

Building a Dendrimer Around (Pd)MCTBP

Dendrimers can be grown from any multi-substituted core, such as a multi-substituted porphyrins, with their different respective properties merging with increase of polymer layers. A divergent dendritic growth scheme example in accordance with this invention is conveniently shown as built around that of a functional (Pd)MCTBP core. While a convergent growth scheme is also contemplated, divergent growth is preferred as it appears to allow for more economical use of PdMCTBP and for more convenient measurements of optical and quenching properties on each step of modification. Once the necessary protection of the porphyrin is achieved, as measured by oxygen quenching constant, the addition of extra layers is not necessary; a finished probe molecule having the desired optimal size is easily synthesized.

In the present invention, any one of several known monomeric units for the formation of divergent dendrimers are useful, such as, for example, as described in U.S. Pat. Nos. 4,507,466; 4,631,337; 4,558,120; 4,568,737 and 4,587,329, and in Tomalia et al. *Angewandte Chemie*, Int. Ed. Eng. 29: 138–175 (1990) and Tomalia et al. *MacroMolecules*, 19: 2466–2468 (1986), the entire disclosures of which are incorporated herein by reference. Other monomeric units suitable for use in the present invention for carrying dendrimer growth around a porphyrin core can be, for example, α, ε-L-lysine described in U.S. Pat. No. 4,289,872 and 1,3-diaminopropan-2-ol in combination with suitable α, β-unsaturated carbonyl compound, such as described in Twyman et al., *Perkin Trans.* 1:407–411 (1994), which are incorporated herein by reference.

Figure 5:
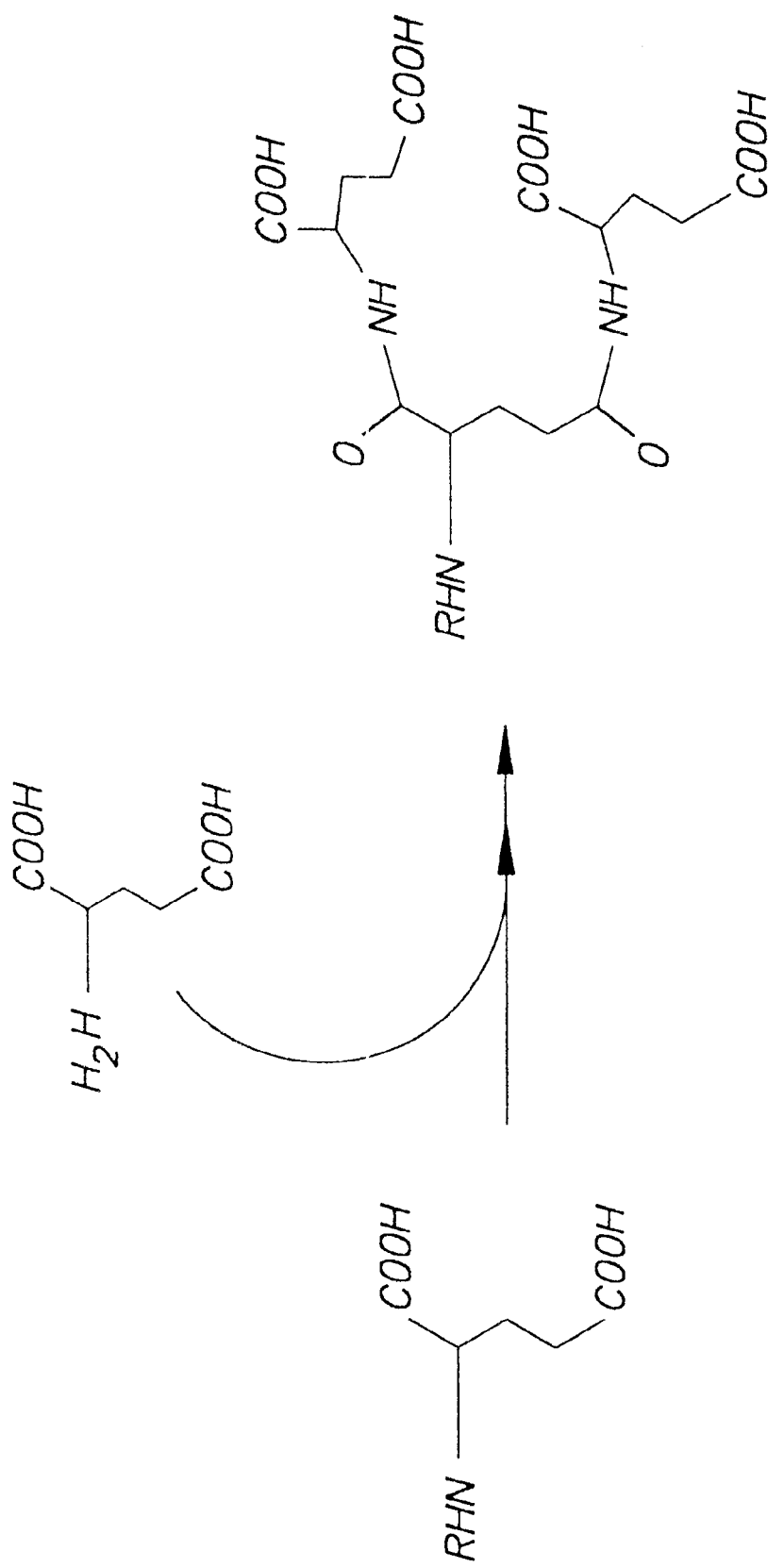
FIG. 5 illustrates the occurrence of branching in a divergent dendrimer growth mode through amide linkages formed using glutamic acid.

In a preferred embodiment of the invention, glutamic acid diallyl ester (diallylglutamate) is employed as a monomeric unit for the modification of PdMCTBP. Diallylglutamate has two protected carboxylic groups and one amino group as shown in FIG. 5. Branching and dendritic polymer formation occurs through formation of amide linkages of each step of polymer formation. It is noted that the reaction scheme in FIG. 5 is drawn for simplicity reasons, and only illustrates non-protected glutamic acid, and not diallyl-glutamate.

The reaction between the carboxyl functionalities of the porphyrin PdMCTBP (Pd-meso-tetra-(4-carboxyphenyl) porphyrin) and diallylglutamate proceeds smoothly in THF at room temperature in the presence of a 1.2 molar excess of DCCD, to produce the corresponding tetraamide in practically quantitative yield.

Figure 6:
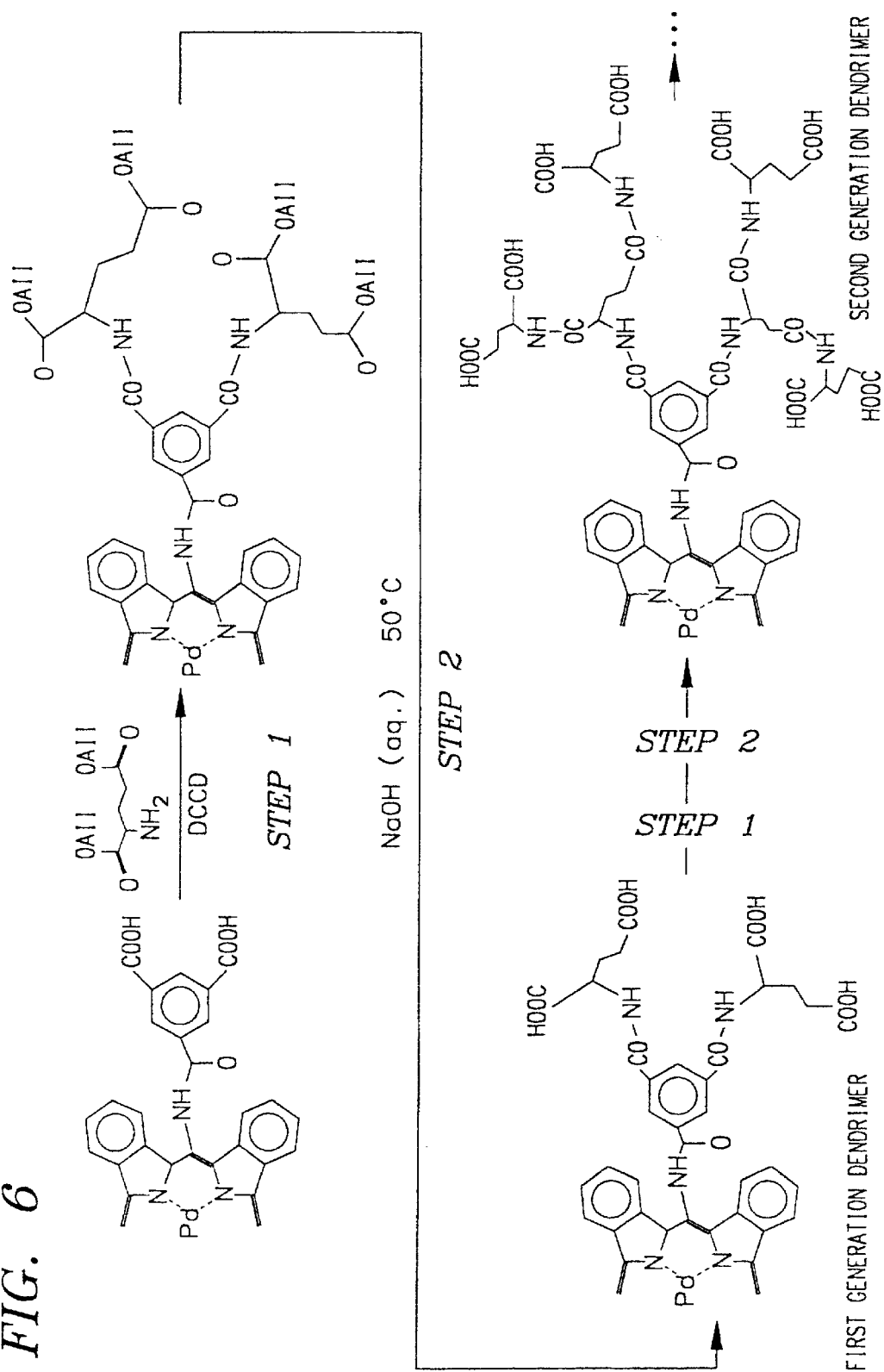
FIG. 6 illustrates a preferred embodiment of the invention of divergent dendrimer growth through two generations using MCTBP or its derivative PdMCTBP as a core porphyrin and diallylglutamate as a monomeric unit.

The allylic moiety on the introduced carboxylic groups can be readily removed by treatment of the ester with warm aqueous NaOH. Amide linkages are completely stable under these reaction conditions. Thus, hydrolysis gives porphyrin with twice as many carboxyl groups, which is ready for the addition of a new glutamate layer, or a second generation. The two first stages of the overall reaction process are shown in FIG. 6. Step 1 denotes amide linkage formation, while Step 2 denotes base catalyzed hydrolysis of the allyl ester protective groups. Purification of the final reaction product can be achieved using membrane filtration, dialysis and size exclusion chromatography, such as successfully employed for the purification of "caged" Zn porphyrin. See Jin et al., *J Chem. Soc. Chem. Commun.* 1260–1262 (1993).

As mentioned above, other monomeric units can be employed for dendrimer formation. These units can have protected functional groups suitable for formation of ester or ether linkages, such as frequently used in convergent dendrimer growth schemes and which are described in Hawker et al., *J. Am. Chem. Soc.* 112: 7683–7647 (1990); and *J. Am. Chem. Soc.* 114: 8405–8413 (1992) Wooly et al., *J. Chem. Soc., Perkin Trans.* 1: 1059–1076 (1991), (1992), the entire disclosures of which are incorporated herein by reference.

Figure 7:
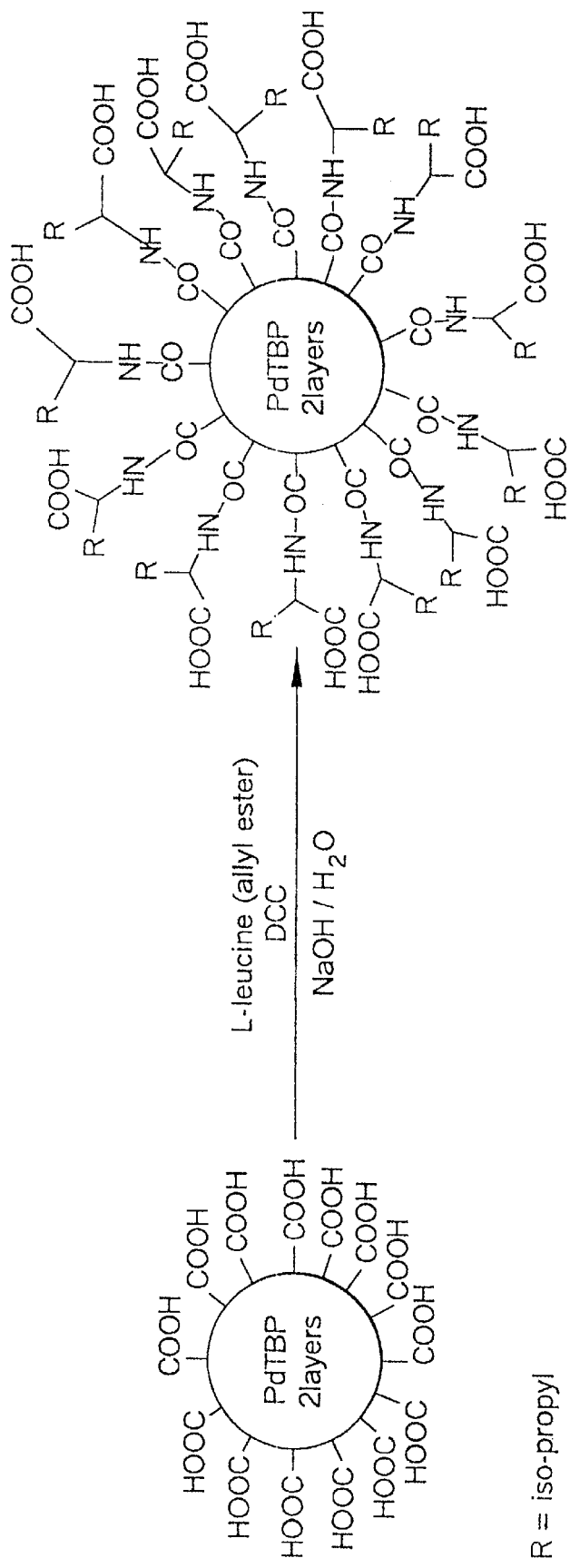
FIG. 7 illustrates a preferred embodiment of the invention of the modification of an outer layer of dendritic porphyrin.
Figure 8:
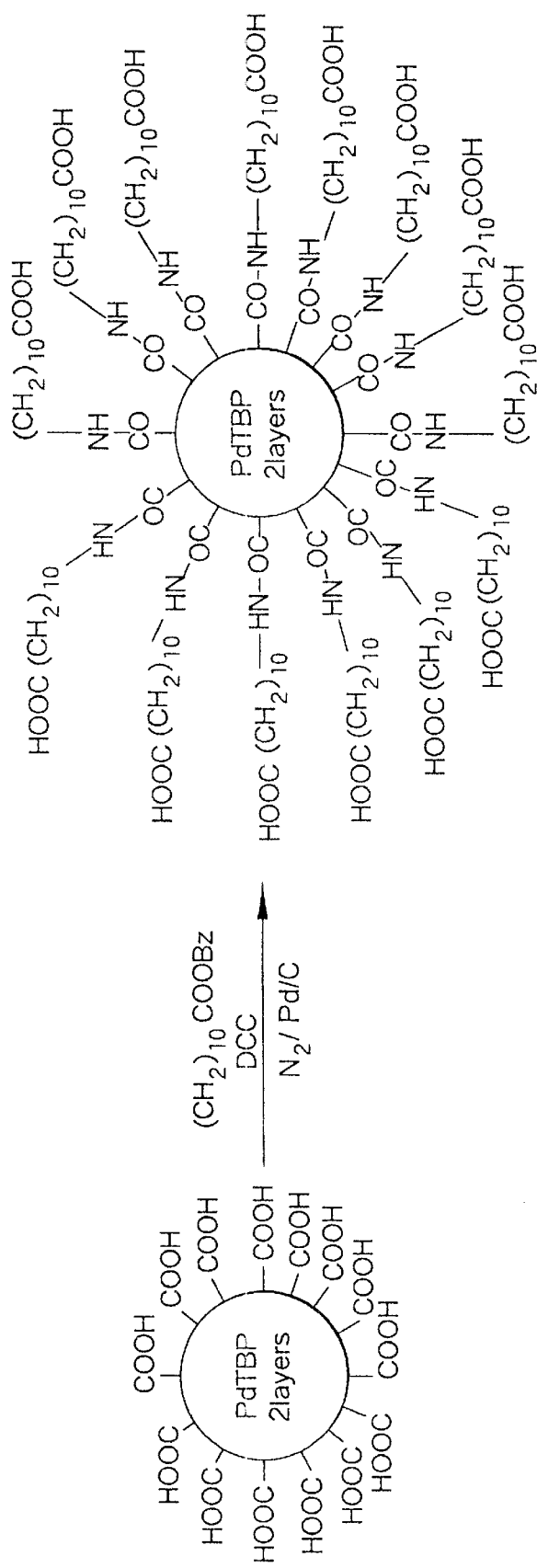
FIG. 8 illustrates another preferred embodiment of the invention of the modification of an outer layer of dendritic porphyrin.

In a further aspect of the present invention, it has been found that modification of the outer layer of dendritic porphyrins with various hydrophobic groups improves protection of core porphyrins. While not wishing to limit any aspect or portion of this invention to theory, it is thought that the addition of surface hydrophobic groups causes formation of more compact structures in water solutions, thereby decreasing oxygen quenching constants. It is also thought that hydrophobic interactions within relatively loosely packed polyamide dendrimer causes it to shrink into smaller ball-like structures of high density which prevent or at least decrease the rate of diffusion of oxygen molecules to the porphyrin core. As illustrated, for example in FIG. 7, significant protection of porphyrin can be achieved when 2-layered polyglutamate dendrimer is surface modified with L-leucine. Furthermore, lower quenching constants are observed for 2-layered polyglutamate modified with sixteen 11-aminoundecanoic acid residues. See FIG. 8.

Toxicity Testing

Phosphor toxicity evaluation for individual candidates in accordance with the invention can be conveniently carried out with the following protocol.

Phosphor powder, Pd-meso-tetra (4-carboxyphenyl) porphyrin with two layers of gultamate dendrimer, was dissolved in five milliliters of distilled, deionized and filter sterilized water through an 0.2 mM filter to provide a solution with a concentration of 8 mM and a pH of 7.4 to provide final dilutions with concentrations in the culture medium of 4,8 and 16 micro-molar.

The three dilutions are made to create stock solutions and to add an equal amount of phosphor solution into each test tube. Control tubes are supplied with the same amount of sterile water.

Each of the final phosphor dilutions (1:500 1:100 and 1:2000) was prepared in duplication. Paired tubes are inoculated with two difference concentrations of *Mycobacterium tuberculosis* culture: 1,000,000 cells/ml and 10,000 cells/ml. Same bacterial concentrations are inoculated into no-phosphor control tubes. In addition, three noninoculated tubes are set up with just phosphor dilutions as a negative control.

All of the higher inoculum tubes turned positive on day 5 of incubation (both with and without phosphor) and the low inoculum tubes became positive on day 7 (with and without phosphor). Noninoculated control tubes remained sterile.

This shows that the phosphor in given concentrations does not affect growth of *M. tuberculosis* in liquid medium tested.

Phosphorimeters

In a preferred mode, excitation light is used which is ulated sinusoidally at a frequency of from 20 to 20,000 Hz. This light source can be any of several difference sources and the modulation can be either direct modulation of the light source or passing the light through a modulation device such as a rotating wheel with slots for the light to pass through. In the preferred mode the light source is a light-emitting diode (LED) or a laser diode, where the latter is a special case of the former. These solid state light sources can be readily modulated at the desired frequency and are monochormatice, i.e., light emission occurs primarily in either a broad band (up to about 60 nm bandwidth at halfheight for LEDs0 or a narrow band of 1 nm or less (for laser diodes). As a result, little optical filtering is required for optimal application to this type of measurement of phosphorescence lifetimes.

What is claimed is:

1. A method for detecting growth or metabolism of microorganisms in an aqueous culture medium, wherein the culture medium comprises a dissolved oxygen-quenchable phosphorescent compound, and wherein the method comprises:

inoculating said culture medium with a sample comprising the microorganisms, exciting the phosphorescent compound dissolved in the medium to phosphoresce, and detecting quenching of the phosphorescence by oxygen in the culture medium, wherein said quenching is indicative of growth or metabolism of the microorganisms.

2. The method of claim 1 wherein said oxygen-quenchable phosphorescent compound is a porphyrin compound having the formula (I)

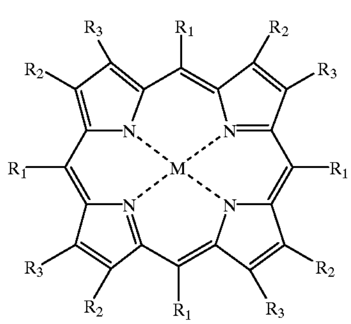

wherein:

$R_1$ is a hydrogen atom or a substituted or unsubstituted aryl;

$R_2$ and $R_3$ are independently hydrogen or are linked together to form substituted or unsubstituted aryl; and M is $H_2$ or a metal.

3. The method of claim 2 wherein in said compound M is a metal selected from the group consisting of Zn, Al, Sn, Y, La, Lu, Pd, and Pt.

4. The method of claim 2 wherein the porphyrin is selected from the group consisting of tetrabenzoporphyrin, tetranaphthoporphyrin, tetraanthraporphyrin, and derivatives thereof.

5. The method of claim 4 wherein in said compound the metal is selected from the group consisting of Zn, Al, Sn, Y, La, Lu, Pd, and Pt.

6. The method of claim 5 wherein said compound is a meso-tetraphenylated compound.

7. The method of claim 6 wherein the metallo-porphyrin is tetraphenyltetrabenzoporphyrin.

8. The method of claim 6 wherein the metalloporphyrin is (Lu) tetraphenyltetranaphthoporphyrin.

9. The method of claim 6 wherein the metalloporphyrin is meso-tetra-(4-carboxylphenyl)porphyrin.

10. The method of claim 6 which is meso-tetraphenyltetrabenzoporphyrin.

11. The method of claim 4 which is meso-tetraphenyltetranaphthoporphyrin.

12. The method of claim 4 wherein the porphyrin is tetrabenzoporphyrin.

13. The method of claim 6 wherein said compound is a first, second, third, fourth or fifth generation dendrimer.

14. The method of claim 13 wherein said dendrimer comprises polyglutamate dendritic cages.

15. The method of claim 1 wherein said microorganism is selected from the group consisting of species from the genera Bacillus, Mycobacterium, Actinomyces, Nocardia, Pseudomanas, Methanomonas, Protaminobacter, Methylococcus, Arthrobacter, Methylomonas, Brevibacterium, Acetobacter, Micrococcus, Rhodopseudomonas, Corynebacterium, Microbacterium, Achromobacter, Methylobacterium, Methylosinum, Methylocystis, Acinetobacter, and mixtures thereof.

16. The method of claim 1, wherein said microorganism is selected from the group consisting of the tuberculosis agents *Mycobacterium tuberculosis, M. boris* and *M. avium.*

17. The method of claim 1 wherein said culture medium is selected from a broth or a gel.

18. The method of claim 1 wherein said culture medium is a fermentation process.

* * * * *